(12) United States Patent
Will et al.

(10) Patent No.: US 8,614,071 B2
(45) Date of Patent: Dec. 24, 2013

(54) PREFERENTIAL AMPLIFICATION OF MRNA OVER DNA USING CHEMICALLY MODIFIED PRIMERS

(75) Inventors: Stephen Will, Cham (CH); Lori Steiner, Alameda, CA (US); Alison Tsan, Castro Valley, CA (US); Nicolas Newton, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 296 days.

(21) Appl. No.: 12/962,890

(22) Filed: Dec. 8, 2010

(65) Prior Publication Data

US 2011/0312040 A1 Dec. 22, 2011

Related U.S. Application Data

(60) Provisional application No. 61/285,678, filed on Dec. 11, 2009.

(51) Int. Cl.
*C12P 19/34* (2006.01)
*C07H 21/00* (2006.01)
*B01L 3/00* (2006.01)

(52) U.S. Cl.
USPC .......................... 435/91.1; 536/23.1; 422/430

(58) Field of Classification Search
USPC .......................... 435/91.1; 536/23.1; 422/430
See application file for complete search history.

(56) References Cited

U.S. PATENT DOCUMENTS

| | | | |
|---|---|---|---|
| 5,137,806 A | 8/1992 | Le Maistre et al. | |
| 5,210,015 A | 5/1993 | Gelfand et al. | |
| 5,521,301 A | 5/1996 | Wallace et al. | |
| 5,595,890 A | 1/1997 | Newton et al. | |
| 5,639,611 A | 6/1997 | Wallace et al. | |
| 5,990,303 A | 11/1999 | Seela | |
| 6,001,611 A | 12/1999 | Will | |
| 7,135,291 B2 | 11/2006 | Sagawa et al. | |
| 7,408,051 B2 | 8/2008 | Ma et al. | |
| 2003/0170637 A1 | 9/2003 | Pirrung et al. | |
| 2010/0099110 A1 | 4/2010 | Will et al. | |

FOREIGN PATENT DOCUMENTS

| | | |
|---|---|---|
| DE | 19935767 A1 | 7/1999 |
| EP | 0974672 B1 | 4/2003 |
| EP | 2009007463 | 2/2010 |
| WO | 0043544 A1 | 7/2000 |
| WO | 0175139 A1 | 10/2001 |
| WO | 2007127992 A2 | 11/2007 |
| WO | 2007127992 A3 | 11/2007 |
| WO | 2010059323 A2 | 5/2010 |
| WO | 2010059323 A3 | 5/2010 |
| WO | PCTEP2010007559 | 6/2011 |

OTHER PUBLICATIONS

Andre, Paulo, et al., 1997, "Fidelity and Mutational Spectrum of Pfu DNA Polymerase on a Human Mitochondrial DNA Sequence", Genome Res., 7:843-852.

Applied Biosystems, 2009, "Avoiding DNA Contamination in RT-PCR (Technical Bulletin #176)", http//www.ambion.com/techlib/tb/tb_176.html.

(Continued)

*Primary Examiner* — Jezia Riley
(74) *Attorney, Agent, or Firm* — David J. Chang

(57) ABSTRACT

The present invention relates to a method, oligonucleotides, reaction mixtures and kits for the selective amplification of a messenger RNA target comprising an exon-exon junction, using an oligonucleotide that comprises at least one nucleotide modified at the exocyclic amino group.

7 Claims, 11 Drawing Sheets amplification curve using primer SEQ ID No: 3

(56) References Cited

OTHER PUBLICATIONS

Figalgo De Silva, Elizabeth, et al., 2007, "DNA polymerase proofreading: active site switching catalyzed by the bacteriophage T4 DNA polymerase", Nucleic Acids Research, 35(16):5452-5463.

Gaster, Jens, et al., 2005, "Tuning Single Nucleotide Discrimination in Polymerase Chain Reactions (PCRs): Synthesis of Primer Probes Bearing Polar 4'-C-Modifications and Their Application in Allele-Specific PCR", Chemistry: a European Journal, 11:1861-1870.

Goodman, Myron F., et al., 1993, "Biochemical Basis of DNA Replicon Fidelity", Critical Reviews in Biochemistry and Molecular Biology, 28(2):83-126.

Newton, C. R., et al., 1989, "Analysis of any point mutation in DNA. The amplification refractory mutation system (ARMS)", Nucleic Acids Research, 17(7):2503-2516.

Reddy, Michael K., et al., 1992, "Processive Proofreading Is Intrinsic to T4 DNA Polymerase", The Journal of Biological Chemistry, 267(20):14157-14166.

Strerath, M. et al., 2007, "Modified Oligonucleotides as Tools for Allele-Specific Amplification", Methods Mol Biol., 402:317-28.

Tews, B. et al., 2003, "Application of the C4'-alkylated deoxyribose primer system (CAPS) in allele-specific real-time PCR for increased selectivity in discrimination of single nucleotide sequence variants", Biol Chem., 384 (10-11):1533-41.

Tindall, Kenneth R., et al., 1988, "Fidelity of DNA Synthesis by the *Thermus aquaticus* DNA Polymerase", Biochemistry 27:6008-6013.

Witcombe, David, et al., 1999, "Detection of PCR products using self-probing amplicons and fluorescence", Nature Biotechnology, 17:804-807.

Bridle, Andrew, R., et al., 2006, "Quantitation of immune response gene expression and cellular localisation of interleukin-1beta mRNA in Atlantic Salmon, *Salmo salar* L., affected by amoebic gill disease (AGD)", Verterinary Immunology and Immunopathology, 114:121-134.

Sandhu, Kuljeet, et al., 2005, "ExPrimer: to design primers from exon-exon-junctions", Bioinformatics, 21 (9):2091-2092.

Stathopoulou, Aliki, et al., 2006, A highly specific real-time RT-PCR method for the quantitative determination of CK-19 mRNA positive cells in peripheral blood of patients with operable breast cancer, International Journal of Cancer, 119:1654-1659.

Primer that spans exon-exon junction amplification curve using primer SEQ ID No: 3 amplification curve using primer SEQ ID No: 6 amplification curve using primer SEQ ID No: 7 amplification curve using primer SEQ ID No: 10 amplification curve using primer SEQ ID No: 11 an amplification curve using primer SEQ ID No: 12 amplification curve using primer SEQ ID No: 13 amplification curve using primer SEQ ID No: 14 amplification curve using primer SEQ ID No: 15

SEQUENCE LISTING

<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (21)..(21)
<223> OTHER INFORMATION: t-butyl-benzyl-dA

<400> SEQUENCE: 1
cagtacccct gccctctgag a                                              21

<210> SEQ ID NO 2
<211> LENGTH: 21

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2 cccctgacc tgcagccccc a                                              21

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(26)
<223> OTHER INFORMATION: t-butyl-benzyl-dA

<400> SEQUENCE: 3
gaacatctgg ctggttcaca tattca                                        26

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
catctggctg gttcacatat tcag                                          24

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
catctggctg gttcacatat tcagg                                         25

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctggctggtt cacatattca ggc                                           23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tggctggttc acatattcag gct                                           23
```

```
<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggctggttca catattcagg ctg                                          23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctggttcac atattcaggc tgg                                          23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(22)
<223> OTHER INFORMATION: t-butyl-benzyl-dC

<400> SEQUENCE: 10
tggctggttc acatattcag gc                                           22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(18)
<223> OTHER INFORMATION: t-butyl-benzyl-dC
<220> FEATURE:
<221> NAME/KEY: modified_base
<222> LOCATION: (22)..(22)
<223> OTHER INFORMATION: t-butyl-benzyl-dC

<400> SEQUENCE: 11
tggctggttc acatattcag gc                                           22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tggctggttc acatattyag gc                                           22

<210> SEQ ID NO 13
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(18)
<223> OTHER INFORMATION: t-butyl-benzyl-dC

<400> SEQUENCE: 13
tggctggttc acatattcag gc                                                22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(19)
<223> OTHER INFORMATION: t-butyl-benzyl-dA

<400> SEQUENCE: 14
tggctggttc acatattcag gc                                                22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(19)
<223> OTHER INFORMATION: t-butyl-benzyl-dA
<220> FEATURE:
<221> NAME/KEY: modified_base
<222> LOCATION: (22)..(22)
<223> OTHER INFORMATION: t-butyl-benzyl-dC

<400> SEQUENCE: 15
tggctggttc acatattcag gc                                                22
```

PREFERENTIAL AMPLIFICATION OF MRNA OVER DNA USING CHEMICALLY MODIFIED PRIMERS

CROSS REFERENCE TO RELATED INVENTION

This application claims the benefit of priority of U.S. Provisional Patent Application Ser. No. 61/285,678, filed Dec. 11, 2009, which is incorporated herein by reference in its entirety.

REFERENCE TO SEQUENCE LISTING

This application contains a Sequence Listing submitted as an electronic text file named "26422US1.txt", having a size in bytes of 5 kb, and created on Dec. 1, 2010. The information contained in this electronic file is hereby incorporated by reference in its entirety pursuant to 37 CFR §1.52(e)(5).

FIELD OF THE INVENTION

The present invention relates to the field of nucleic acid amplification and more specifically, to the field of RNA amplification by reverse-transcription polymerase chain reaction (RT-PCR).

BACKGROUND OF THE INVENTION

Reverse-transcription polymerase chain reaction is a method of generating and exponentially amplifying DNA copies of an RNA template. The method has both qualitative and quantitative applications in the field of gene expression. The method allows to both detect and measure the levels of mRNA expressed by an organism.

The principal difficulty with RT-PCR is contamination of RNA preparations with genomic DNA. As admitted by the leading distributor of RNA isolation reagents and technologies, most RNA isolation techniques yield RNA with significant amount of genomic DNA contamination. (Ambion, Austin, Tex., (Life Technologies, Inc.), Technical Bulletin #176 "Avoiding DNA contamination in RT-PCR.") DNA contamination is especially problematic for RT-PCR, where the smallest amount of contaminating DNA will be exponentially amplified. One method of reducing the amplification of DNA by RT-PCR involves pre-treating the samples with deoxyribonuclease, such as DNase I, see Huang, et al. (1996) *Biotechniques* 20:1012-1020. Unfortunately, this approach is not without problems. After pre-treatment, the DNase must be completely inactivated in order to prevent digestion of the nascent DNA amplicons in the course of RT-PCR. However, high temperatures necessary for compete inactivation of the DNAse cause degradation of the RNA template. As an alternative to heating, one may chemically remove the DNase by phenol extraction or using various elaborate and costly reagents that remove DNase from the reaction mixture. In summary, the use of DNase is impractical in RT-PCR as it requires multiple additional steps and often threatens the fragile RNA target.

Since the problem of DNA contamination is considered intractable, efforts have been devoted to preventing amplification of the DNA contaminant by RT-PCR. One such strategy takes advantage of the presence of introns in eukaryotic genomic DNA. In mature mRNA, the introns are absent. If the primers are designed to flank an intron, the intron will be absent from the amplicon generated from mRNA. However, the intron will be included in the RT-PCR amplicon generated from the corresponding genomic DNA template. If the intron is sufficiently large, the shorter mRNA sequence (and subsequently the cDNA sequence) will be preferentially amplified, while the genomic DNA will be amplified less efficiently or not at all (Ambion, Tech. Bull. #176). In the worst case scenario, the genomic DNA will be co-amplified with the desired mRNA target, but the two amplicons will be distinguishable by electrophoresis.

Unfortunately, primer design is not always capable of overcoming the problem of DNA contamination. Many PCR tests now involve real-time PCR, a technique that does not include electrophoresis but is able to detect nucleic acids simultaneously with amplification, see U.S. Pat. Nos. 5,994,056 and 5,876,930 and related patents. Without electrophoresis, real-time PCR is not capable of parsing out different-size amplicons generated with the same set of primers. Any real-time PCR probe that detects an mRNA target will inevitably also detect the corresponding genomic DNA contaminant. An mRNA and its corresponding genomic DNA will not be distinguished. Therefore, where introns in the region of interest are too small to preclude amplification of genomic DNA, real-time PCR may not be used.

It is therefore desirable to create a novel method of primer design that will ensure that genomic DNA contaminants are not co-amplified with mRNA during RT-PCR. Such a primer design method would enable quantitative amplification of mRNA targets regardless of the size of the intron present in the amplicon.

SUMMARY OF THE INVENTION

In a first aspect, the invention relates to a method of selective amplification of a messenger RNA target in a sample, comprising an exon-exon junction, comprising the steps of a) hybridizing a first oligonucleotide to said mRNA target and performing RNA-directed DNA synthesis using at least one enzyme capable of RNA-directed synthesis, wherein said first oligonucleotide comprises at least one nucleotide modified at the exocyclic amino group, is at least partially complementary to said mRNA target, and spans an exon-exon junction in the target; and b) amplifying the product of step a) using said first oligonucleotide and a second oligonucleotide with at least one enzyme capable of DNA-directed DNA synthesis; wherein said second oligonucleotide is at least partially complementary to said mRNA target. Oligonucleotides, reaction mixtures and a kits for practicing the present invention are also disclosed.

DETAILED DESCRIPTION OF THE INVENTION

Definitions

Figure 1:
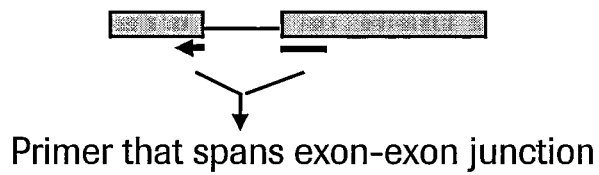
FIG. 1 is a schematic representation of an exon-exon junction as defined hereinafter in the context of the invention.
Figure 2:
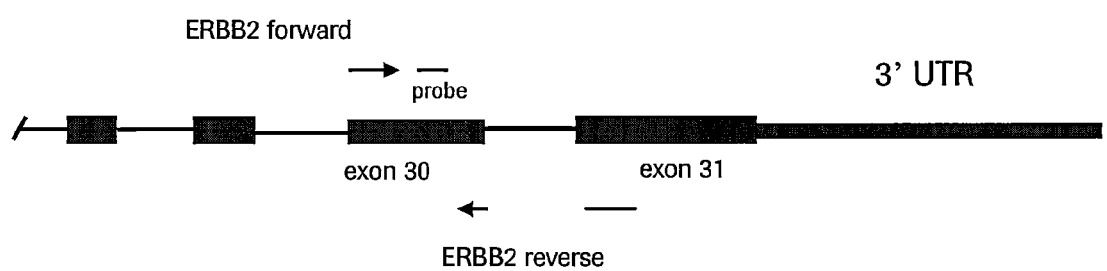
FIG. 2 is a schematic representation of a primer design according to the present invention.
Figure 3:
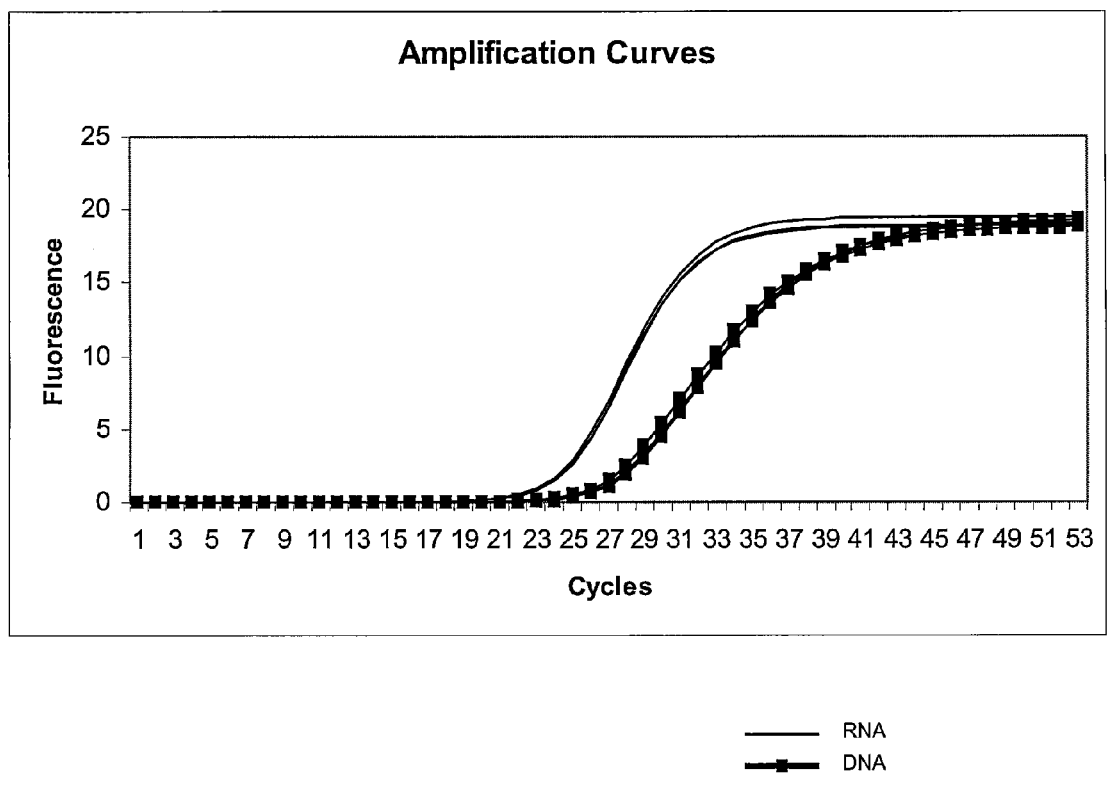
FIG. 3 shows an amplification curve using primer SEQ ID No: 3 used in method according to the present invention.
Figure 4:
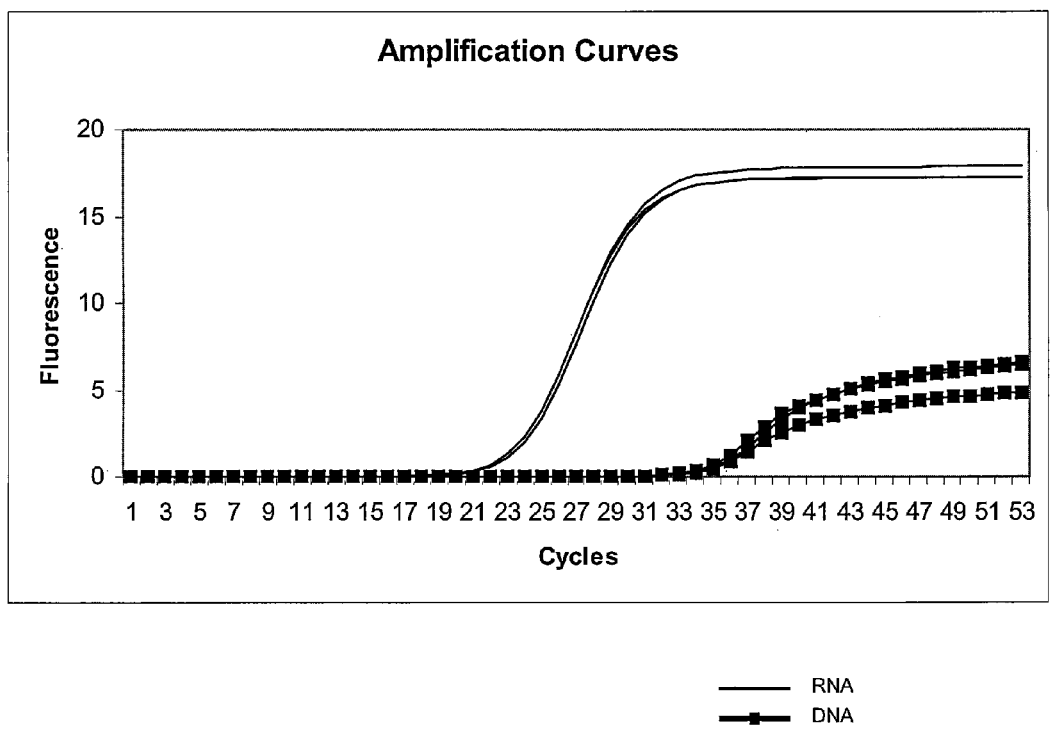
FIG. 4 shows an amplification curve using primer SEQ ID No: 6 used in method according to the present invention.
Figure 5:
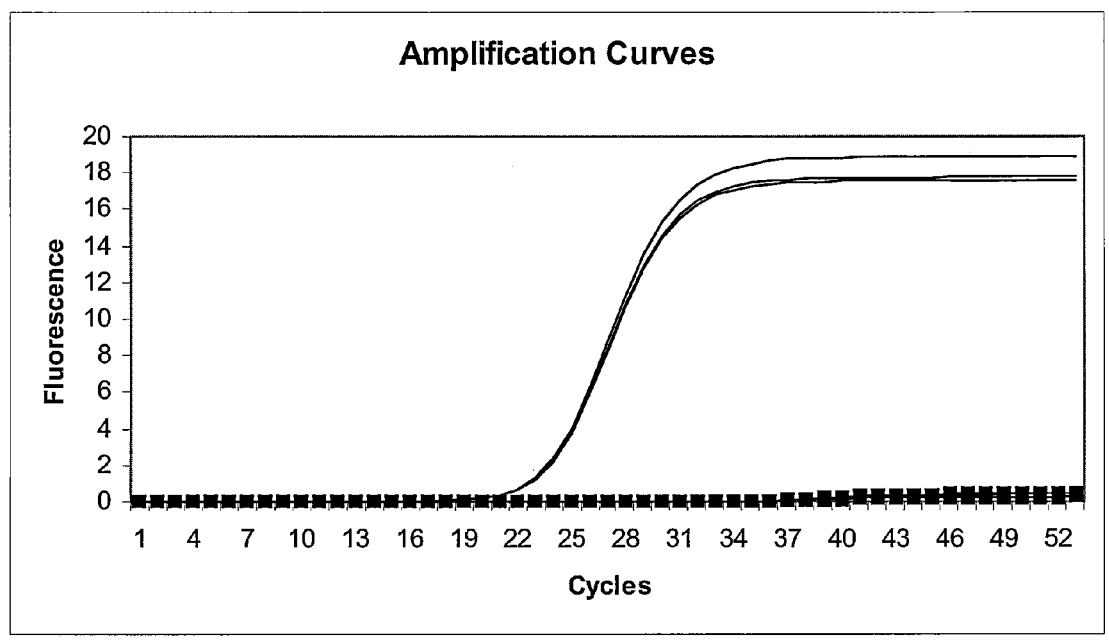
FIG. 5 shows an amplification curve using primer SEQ ID No: 7 used in method according to the present invention.
Figure 6:
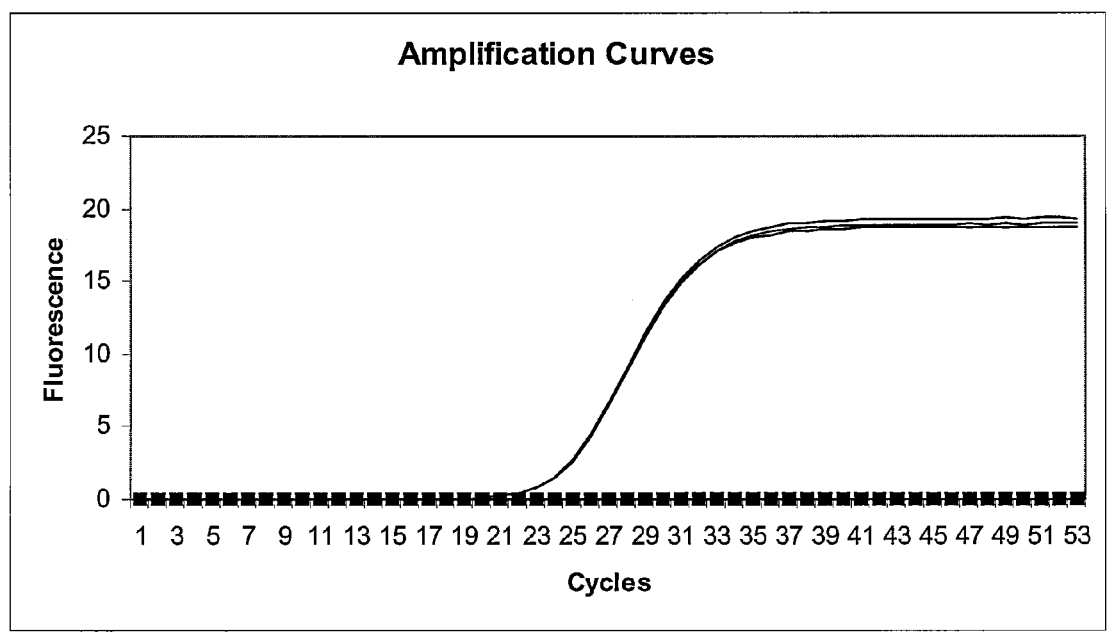
FIG. 6 shows an amplification curve using primer SEQ ID No: 10 used in method according to the present invention.
Figure 7:
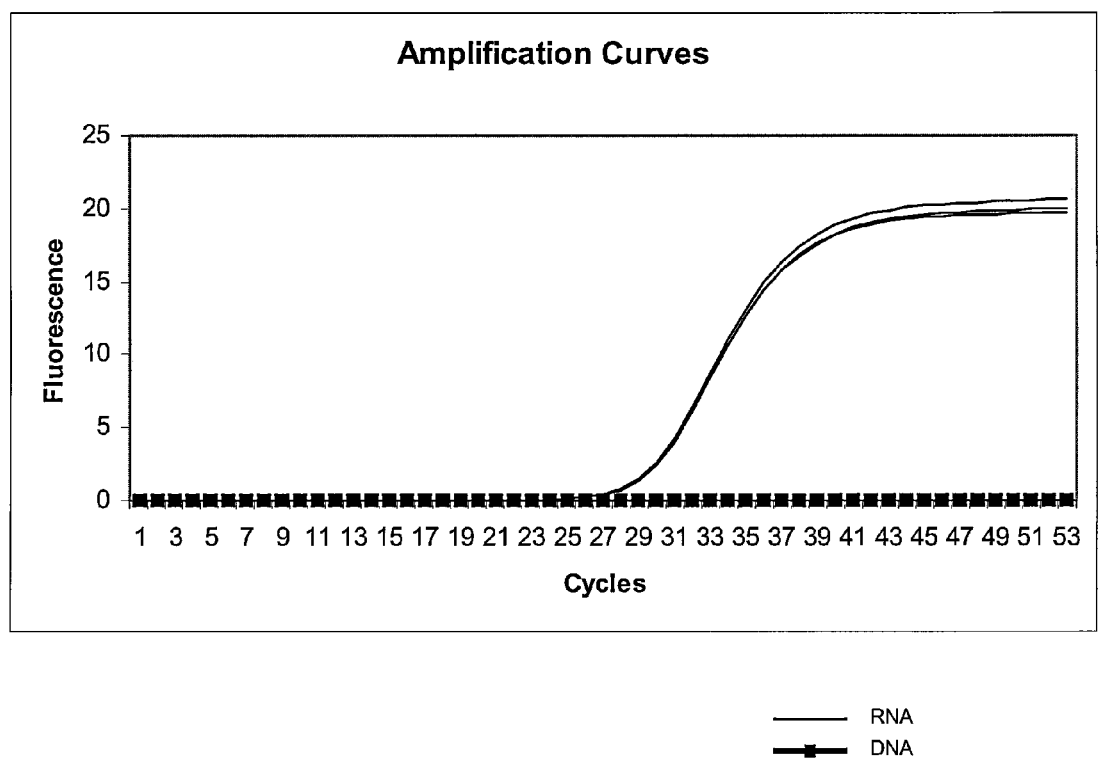
FIG. 7 shows an amplification curve using primer SEQ ID No: 11 used in method according to the present invention.
Figure 8:
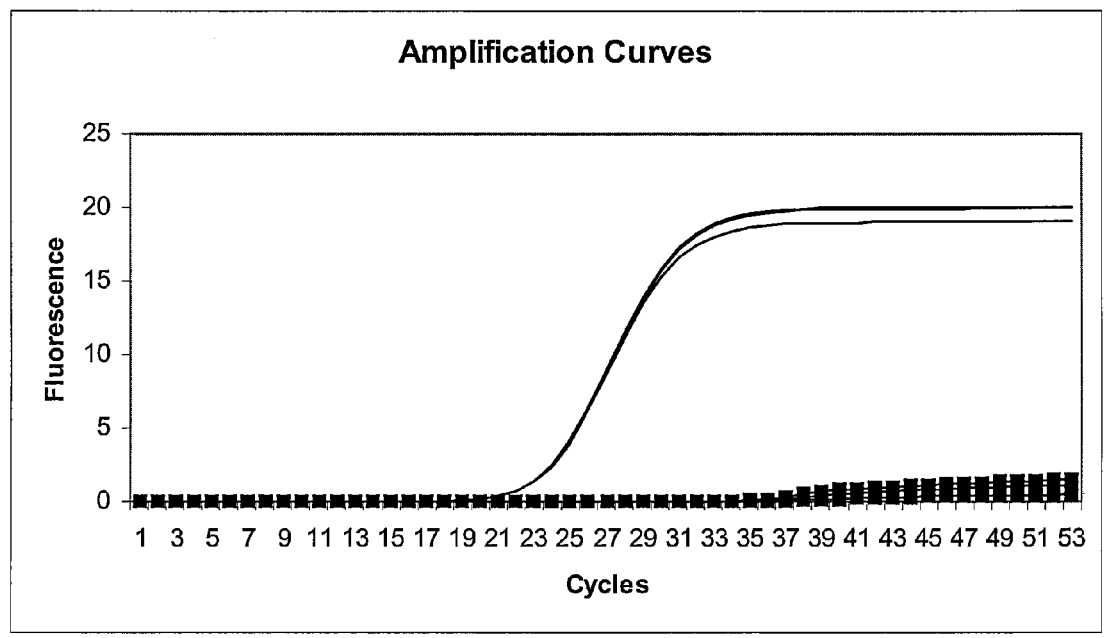
FIG. 8 shows an amplification curve using primer SEQ ID No: 12 used in method according to the present invention.
Figure 9:
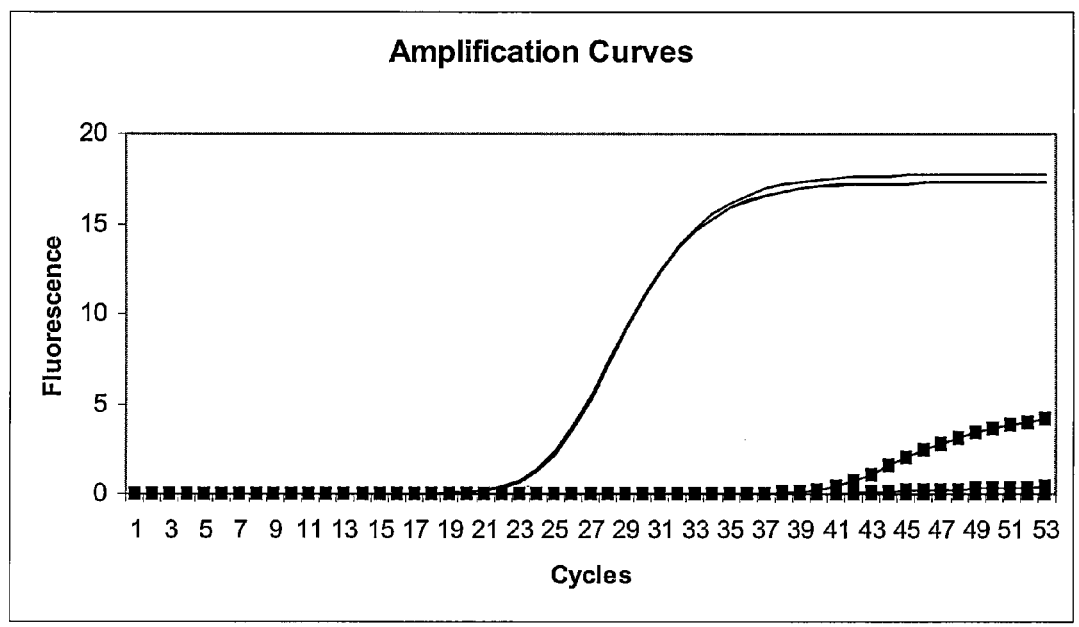
FIG. 9 shows an amplification curve using primer SEQ ID No: 13 used in method according to the present invention.
Figure 10:
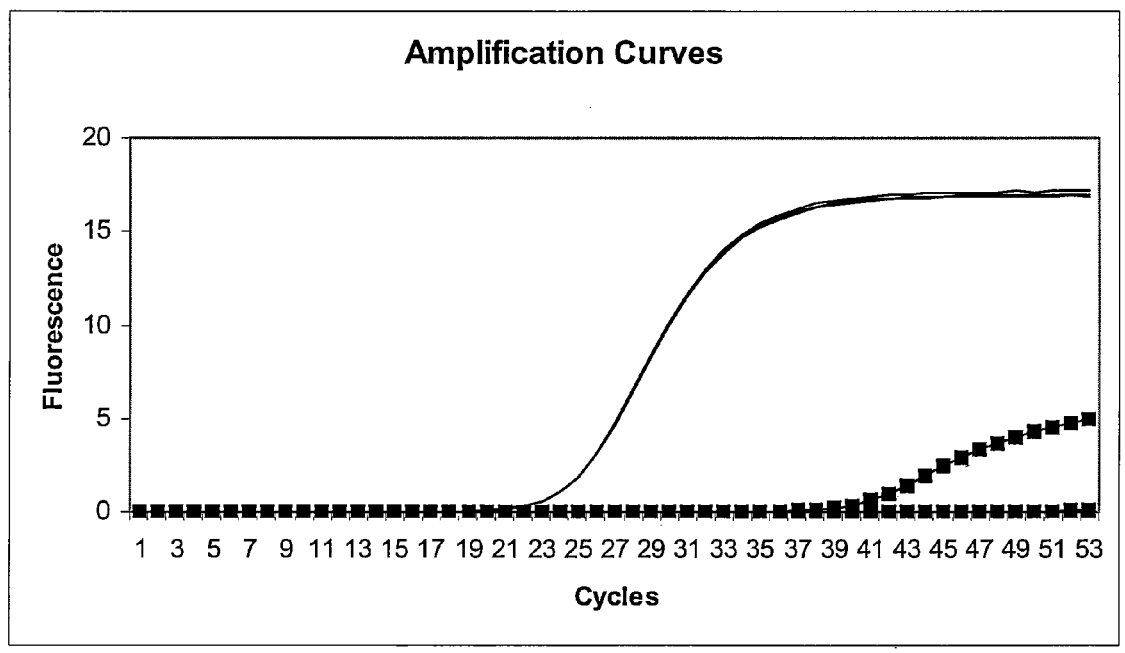
FIG. 10 shows an amplification curve using primer SEQ ID No: 14 used in method according to the present invention.
Figure 11:
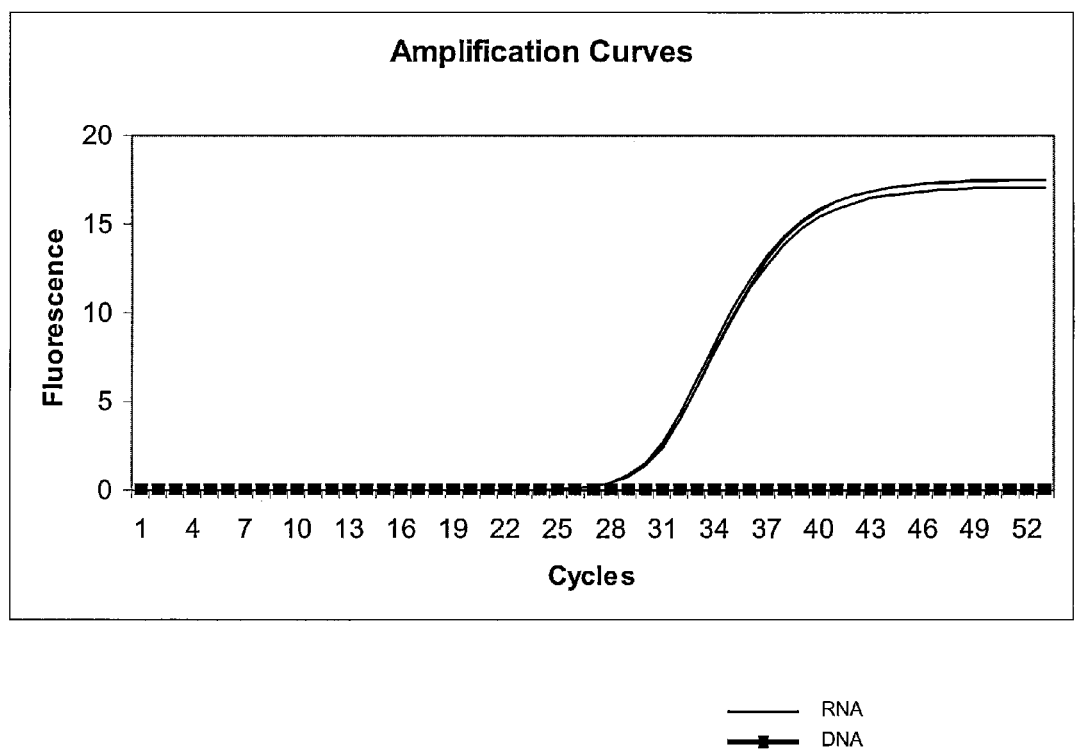
FIG. 11 shows an amplification curve using primer SEQ ID No: 15 used in method according to the present invention.

In describing and claiming the present invention, the following definitions will be used. Unless defined otherwise below, all technical and scientific terms used herein have the same meaning as commonly understood by one of ordinary skill in the art to which this invention pertains.

The term "messenger RNA" or "mRNA" refers to RNA that is transcribed from genomic DNA and that carries the coding sequence for protein synthesis. In eukaryotic organisms, the nucleotide sequence of mRNA is modified in order to form the protein-coding sequence. Typically the modification involves "splicing" or removal of introns from the mRNA sequence. In some instances, the nucleotide sequence of mRNA is also changed by "editing" in order to form the protein-coding sequence.

In the context of mRNA synthesis, the term "corresponding genomic DNA" refers to genomic DNA containing the template for the mRNA in question. Corresponding genomic DNA may contain additional sequences that are similar or complementary to the template for the mRNA, such as the gene in question as well as duplications of that gene and pseudogenes. Typically, corresponding genomic DNA comes from the same organism as the mRNA, however, the corresponding genomic DNA may come from a different organism as in the case of certain viruses. In the case of retroviruses that exist in the form of RNA, the corresponding genomic DNA may be host DNA containing a provirus (integrated viral DNA).

The term "nucleic acid" refers to polymers of nucleotides (e.g., ribonucleotides, deoxyribonucleotides, nucleotide analogs etc.) and comprising deoxyribonucleic acids (DNA), ribonucleic acids (RNA), DNA-RNA hybrids, oligonucleotides, polynucleotides, aptamers, peptide nucleic acids (PNAs), PNA-DNA conjugates, PNA-RNA conjugates, etc., that comprise nucleotides covalently linked together, either in a linear or branched fashion. A nucleic acid is typically single-stranded or double-stranded and will generally contain phosphodiester bonds, although in some cases, nucleic acid analogs are included that may have alternate backbones, including, for example, phosphoramide (Beaucage et al. (1993) *Tetrahedron* 49(10):1925); phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321), O-methylphophoroamidite linkages (see Eckstein, *Oligonucleotides and Analogues: A Practical Approach*, Oxford University Press (1992)), and peptide nucleic acid backbones and linkages (see, Egholm (1992) *J. Am. Chem. Soc.* 114:1895). Other analog nucleic acids include those with positively charged backbones (Denpcy et al. (1995) *Proc. Natl. Acad. Sci. USA* 92: 6097); non-ionic backbones (U.S. Pat. Nos. 5,386,023, 5,637,684, 5,602,240, 5,216,141 and 4,469,863) and non-ribose backbones, including those described in U.S. Pat. Nos. 5,235,033 and 5,034,506. Nucleic acids comprising one or more carbocyclic sugars are also included within the definition of nucleic acids (see Jenkins et al. (1995) *Chem. Soc. Rev.* pp. 169-176), and analogs are also described in, e.g., Rawls, *C & E News* Jun. 2, 1997 page 35. These modifications of the ribose-phosphate backbone may be done to facilitate the addition of additional moieties such as labels, or to alter the stability and half-life of such molecules in physiological environments.

In addition to the naturally occurring heterocyclic bases that are typically found in nucleic acids (e.g., adenine, guanine, thymine, cytosine, and uracil), nucleic acids also may include nucleotide analogs with non-naturally occurring heterocyclic bases, such as those described in, e.g., Seela et al. (1999) *Helv. Chim. Acta* 82:1640. Certain bases used in nucleotide analogs act as melting temperature ($T_m$) modifiers. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303. Other representative heterocyclic bases include, e.g., hypoxanthine, inosine, xanthine and their derivatives.

A "nucleoside" refers to a nucleic acid component that comprises a base or basic group (comprising at least one homocyclic ring, at least one heterocyclic ring, at least one aryl group, and/or the like) covalently linked to a sugar moiety, a derivative of a sugar moiety, or a functional equivalent of a sugar moiety (e.g. a carbocyclic ring). For example, when a nucleoside includes a sugar moiety, the base is typically linked to a 1'-position of that sugar moiety. As described above, a base can be a naturally occurring base or a non-naturally occurring base. Exemplary nucleosides include ribonucleosides, deoxyribonucleosides, dideoxyribonucleosides and carbocyclic nucleosides.

A "nucleotide" refers to an ester of a nucleoside, e.g., a phosphate ester of a nucleoside, having one, two, three or more phosphate groups covalently linked to the sugar moiety or its derivative or equivalent.

An "oligonucleotide" refers to a nucleic acid that includes at least two, but typically 5-50 nucleotides and more typically, between 15 and 35 nucleotides. The exact size of an oligonucleotide generally depends on various factors, including the ultimate function or use of the oligonucleotide. Oligonucleotides may be prepared by any suitable method known in the art, including, for example, cloning and restriction digestion of appropriate sequences, or direct chemical synthesis by a method such as the phosphotriester method of Narang et al. (1979) *Meth. Enzymol.* 68:90-99; the phosphodiester method of Brown et al. (1979) *Meth. Enzymol.* 68:109-151; the diethylphosphoramidite method of Beaucage et al. (1981) *Tetrahedron Lett.* 22:1859-1862; the triester method of Matteucci et al. (1981) *J. Am. Chem. Soc.* 103: 3185-3191; automated synthesis methods; the solid support method of U.S. Pat. No. 4,458,066 or any other chemical method known in the art.

A "primer" is an oligonucleotide that can hybridize to a template nucleic acid and permit chain extension or elongation using a nucleotide incorporating enzyme. Although other primer lengths are sometimes utilized, primers typically range from 15 to 35 nucleotides. Short primers generally utilize cooler temperatures to form sufficiently stable hybrid complexes with template nucleic acids. A primer that is at least partially complementary to a subsequence of a template nucleic acid is typically sufficient to hybridize with the template nucleic acid for extension to occur. However, the success of the extension generally requires greater complementarity (i.e. fewer mismatches with the template) at the 3'-end of the primer. A primer can be labeled, if desired, by incorporating a label detectable by radiological, spectroscopic, photochemical, biochemical, immunochemical, or chemical techniques.

"Primer extension" is the action of the enzyme by which additional nucleotides are added to the primer.

A "template nucleic acid", "template" or "target" refers to a nucleic acid to which a primer can hybridize and be extended under suitable conditions. In the context of nucleic acid amplification, "target" is preferably a region of nucleic acid, consisting of the sequences at least partially complementary to at least two primer sequences and the intervening sequence. Templates or target nucleic acids can exist as isolated nucleic acid fragments or be a part of a larger nucleic acid fragment. Target nucleic acids can be derived or isolated from essentially any biological source, such as microorganisms, complex biological mixtures, tissues, sera, including human patient samples or tissues and sera, ancient or preserved tissues or samples, environmental isolates or the like. Further, template nucleic acids optionally include or are derived from cDNA, RNA, genomic DNA, cloned genomic DNA, genomic DNA libraries, enzymatically fragmented DNA or RNA, chemically fragmented DNA or RNA, physically fragmented DNA or RNA, or the like. Template nucleic acids can also be chemically synthesized using techniques known in the art.

A "real-time PCR" assay is a PCR assay wherein the amplicon is detected and quantified in the course of PCR cycles. A typical real-time PCR assay involves optical detection of the amplification product that takes place repeatedly during the cycling. The measure of amplification is the "threshold cycle" or "Ct," a cycle when fluorescence above background is first detected. An earlier Ct value reflects the rapid achievement of the threshold level and thus a higher initial template input or a more efficient amplification. The later Ct value may reflect a smaller amount of initial template input or inefficient or inhibited amplification.

As used herein, a "gene" refers to any segment of DNA associated with a biological function. Thus, genes include coding sequences, intervening non-coding sequences (introns) and optionally, the regulatory sequences required for the expression of the coding sequences.

A "moiety" or "group" refers to one of the portions into which something, such as a molecule, is divided (e.g., a functional group, substituent group, or the like). For example, a nucleotide typically comprises a base group (e.g., adenine, thymine, cytosine, guanine, uracil, or an analog), a sugar moiety, and one or more phosphate groups.

An "alkyl group" refers to a linear, branched, or cyclic saturated hydrocarbon moiety and includes all positional isomers, e.g., methyl, ethyl, propyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, n-hexyl, cyclohexyl, n-heptyl, n-octyl, 2-ethylhexyl, n-nonyl, n-decyl and the like. An alkyl group typically comprises about 1-20 carbon atoms and more typically comprises about 2-15 carbon atoms. Alkyl groups can be substituted or unsubstituted.

An amplification assay is "selective" or "target-selective" if it yields a predominance (i.e., a majority but less than 100%) of one product over other possible products. An assay is described as "selective" as long as amplification of the undesired variant of the target sequence is detectable. The assay where amplification of the undesired target is undetectable is called "specific." As the methods of detection become more sensitive, some assays previously known to be specific, turn out to be merely selective, i.e. some amplification of undesired variants of the target becomes detectable. Therefore, in the context of this invention, the term "specific" is meant to encompass both strictly target-specific, as well as target-selective amplification.

A "complementary nucleic acid" is a nucleic acid or a nucleic acid segment that can hybridize or form a duplex with at least a subsequence of another nucleic acid. Complementarity need not be perfect for a duplex to form, i.e., nucleic acids in a duplex can be "partially complementary". Those skilled in the art of nucleic acid technology can determine duplex stability by empirically considering a number of variables including, for example, the length of a region of complementarity, base composition and sequence of nucleotides in a region of complementarity, ionic strength of the solution of nucleic acids, and incidence of mismatched base pairs.

A term "detectable" with respect to an analyte such as nucleic acid in a sample, means detectable using the state of the art detection methods. It is understood that as the detection methods improve, the currently undetectable levels of analyte may become detectable. Therefore the term "detectable" as used herein denotes the ability to measure the presence or absence of a species using appropriate analytical techniques which are reasonably available and practical within laboratory settings and are known to those skilled in the art.

A "nucleotide incorporating enzyme" refers to an enzyme that catalyzes the incorporation of nucleotides into a nucleic acid. Exemplary nucleotide incorporating enzymes include, DNA polymerases, RNA polymerases, terminal transferases, reverse transcriptases, telomerases and the like.

A "thermostable enzyme" refers to an enzyme that is stable (i.e., resists breakdown or denaturation) and retains sufficient catalytic activity when subjected to elevated temperatures for selected periods of time. For example, a thermostable polymerase retains sufficient activity to effect subsequent primer extension reactions, when subjected to elevated temperatures for the time necessary to denature double-stranded nucleic acids. Heating conditions necessary for nucleic acid denaturation are well known in the art and are exemplified in U.S. Pat. Nos. 4,683,202 and 4,683,195. As used herein, a thermostable polymerase is typically suitable for use in a temperature cycling reaction such as the polymerase chain reaction ("PCR"). The examples of thermostable nucleic acid polymerases include *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, and the like.

A "modified" enzyme refers to an enzyme comprising an amino acid polymer in which at least one monomer differs from the reference sequence, such as a native or wild-type form of the enzyme or another modified form of the enzyme. Exemplary modifications include monomer insertions, deletions, and substitutions. Modified enzymes also include chimeric enzymes that have identifiable component sequences (e.g., structural or functional domains, etc.) derived from two or more parents. Also included within the definition of modified enzymes are those comprising chemical modifications of the reference sequence. The examples of modified polymerases include G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, ΔZ05 polymerase, ΔZ05-Gold polymerase, ΔZ05R polymerase, E615G Taq DNA polymerase, E678G TMA-25 polymerase, E678G TMA-30 polymerase, and the like.

The term "5' to 3' nuclease activity" or "5'-3' nuclease activity" refers to an activity of a nucleic acid polymerase, typically associated with the nucleic acid strand synthesis, whereby nucleotides are removed from the 5' end of nucleic acid strand, e.g., *E. coli* DNA polymerase I has this activity, whereas the Klenow fragment does not.

A polymerase that "substantially lacks 5'-3' nuclease activity" refers to a polymerase that has 50% or less (e.g., <25%, <20%, <15%, <10%) 5'-3' nuclease activity than Taq DNA polymerase. Methods of measuring 5'-3' nuclease activity and conditions for measurement are well known in the art. See, e.g., U.S. Pat. No. 5,466,591. Examples of DNA polymerases substantially lacking 5' to 3' nuclease activity include the Klenow fragment of *E. coli* DNA polymerase I; a *Thermus aquaticus* DNA polymerase (Taq) lacking the N-terminal 235 amino acids (e.g., as described in U.S. Pat. No. 5,616,494 and commonly referred to in the art as the "Stoffel fragment"). Other examples include a thermostable DNA polymerase having sufficient deletions (e.g., N-terminal deletions), mutations, or modifications so as to eliminate or inactivate the domain responsible for the 5'-3' nuclease activity. See, e.g., U.S. Pat. No. 5,795,762.

A "label" refers to a moiety attached (covalently or non-covalently), to a molecule and capable of providing information about the molecule. Exemplary labels include fluorescent labels, colorimetric labels, chemiluminescent labels, bioluminescent labels, radioactive labels, mass-modifying groups, antibodies, antigens, biotin, haptens, and enzymes (including peroxidase, phosphatase, etc.).

An "exon" is a nucleic acid present in genomic DNA and in the mature form of messenger RNA. Exon sequence is a portion of a gene that is translated into protein. Exons commonly contain coding sequences which are parts of the open reading frame (ORF).

The expression "exon-exon junction" refers to a junction between two exons that results from the joining of two exons upon the removal of the intron adjacent to said exons.

The expression "a first oligonucleotide that spans an exon-exon junction in the target" refers to an oligonucleotide that is capable of spanning two exons that are separated by an intro in a target oligonucleotide. FIG. 1 is provided for the sole purpose of illustration. FIG. 1 is a schematic representation of a typical oligonucleotide comprising exons and introns. FIG. 1 shows an example of exon-exon junction in this oligonucleotide and a first oligonucleotide spanning this junction is represented by an arrow. The first oligonucleotide spans the exon-exon junction by hybridizing to the two exons adjacent to the intron, and not to the intron.

An "intron" refers to a nucleic acid present in genomic DNA but not in the mature form of messenger RNA. An intron sequence is a portion of a gene that is not transcribed into RNA nor translated into protein.

"Gene expression" refers to the process by which information from a gene is used in the synthesis of a functional gene product, such as protein or functional RNA. A part of gene expression typically involves copying a portion of genomic DNA molecule into an RNA molecule by the process known as "transcription". Gene expression studies involve studying the RNA or protein synthesized using the information in the gene.

"Reverse transcription" refers to the process of making a double stranded DNA molecule from a single stranded RNA template. Reverse transcription is catalyzed by a nucleic acid polymerase with reverse transcriptase activity.

"Reverse transcription polymerase chain reaction (RT-PCR)" is a variant of polymerase chain reaction (PCR), wherein an RNA strand is first reverse transcribed into its DNA complement (cDNA) and the resulting cDNA is amplified using traditional PCR. RT-PCR requires an enzyme with reverse transcriptase activity and a preferably thermostable enzyme with DNA polymerase activity. In some instances the two activities are present in the same enzyme.

A "hot start", in the context of a nucleic acid amplification reaction, refers to a protocol, where at least one critical reagent is withheld from the reaction mixture (or, if physically present in the reaction mixture, the reagent remains inactive) until the temperature is raised sufficiently to provide the necessary hybridization specificity of the primer or primers. A "hot start enzyme" is an enzyme, typically a nucleic acid polymerase, capable of acting as the "withheld" or inactive reagent in a hot start protocol. Such hot start enzyme can for example be obtained by chemically modifying the enzyme. A non limiting example of such chemically modified enzyme is commercially available Eagle Taq. These hot start enzymes can also be obtained with an antibody or an aptamer that binds to a polymerase, such as it is for example the case in commercially available Hawk Z05.

A term "undetectable" refers to lack of detection by the methods of detecting as practiced at the time of the present invention. It is to be understood that the term "undetectable" does not mean complete absence of a substance for which detection is sought. It means that conventional methods known at the time of the present invention do not allow detection of a substance for which detection is sought.

A term "analytical specificity" refers to the amount of undesired nucleic acid target at which the assay is still specific towards the desired nucleic acid target. For example, in an mRNA amplification assay, "analytical specificity for 1 microgram of genomic DNA" means that when the level of genomic DNA contamination is 1 microgram per reaction, the DNA is not detectably amplified, while the mRNA is detectably amplified.

The present invention provides a method of preferential amplification of messenger RNA in the presence of genomic DNA contaminant using chemically modified primers. The present invention comprises methods, kits and reaction mixtures useful for preferential amplification and detection of mRNA over DNA within samples. The present invention can be used for detecting, identifying and quantifying mRNA from various eukaryotic organisms and tissues of eukaryotic organisms, including patient tissues and samples in clinical applications.

An exemplary application of quantifying mRNA is a gene expression study. Gene expression studies are a part of basic and applied research as well as clinical diagnostics. In clinical applications, the level of messenger RNA may reflect progression of a disease. In drug therapy, the level of mRNA may be reflective of the efficacy of a drug targeting a particular gene expression pathway. For example, treatment with antibodies against the family of EGF receptors results in down-regulation of a number of genes in the EGFR pathway. Tzahar et al., (1998) *Biochim. Biophys. Acta* 1337:M25. The measured changes in expression of the genes in the EGFR pathway are reflective of efficacy of a particular drug.

In a typical study, the total RNA or mRNA would be isolated from a sample and subjected to the nucleic acid analysis procedure of choice. Unfortunately, similarities in chemical properties between RNA and DNA result in co-isolation of RNA and DNA. For some analysis methods, the presence of a small DNA contaminant is acceptable. However, for more sensitive amplification-based methods, such as PCR and RT-PCR, even small amount of DNA may distort the results of the test. In most cases, primers and probes specific for a particular species of RNA hybridize to the corresponding genomic DNA sequence, leading to co-amplification and co-detection of the genomic DNA contaminant. Thus the presence of genomic DNA contaminant would create a false-positive result, falsely indicating gene expression or would distort the quantitative result, indicating incorrect level of gene expression.

The problem of DNA contamination is generally considered intractable, i.e. some DNA will always be present in an RNA preparation. Therefore it is desirable to minimize the effect of the contaminant. In the context of RT-PCR, it is desirable to minimize amplification of the DNA contaminant. As a measure of specificity towards mRNA, each RNA-specific assay may be characterized by analytical specificity, or the amount of genomic DNA contaminant at which the DNA is not detectably co-amplified with the mRNA.

The present invention is a method of selectively amplifying mRNA with clinically acceptable analytical specificity in the presence of genomic DNA. For instance, in an example set out to illustrate but not limit the invention, the analytical specificity is 1 microgram of genomic DNA per reaction. It is recognized that some amplification of the contaminant may occur with the method of the present invention. However, a method would be considered to perform satisfactorily as long as amplification of the DNA contaminant present up to a certain acceptable maximum level is undetectable by the state of the art detection methods employed.

The existing methods of reducing or eliminating amplification of contaminating DNA in an RT-PCR reaction take advantage of the presence of introns. The target mRNA would differ from the corresponding genomic DNA by its lack of intervening sequences or introns. One way to prevent amplification of contaminating genomic DNA is to design amplification primers to flank an intron. If the primers flank an intron, the genomic DNA will yield a product of a different size, or if the intron is prohibitively large, yield no product at all. Unfortunately, in some instances the intron in the sequence of interest is not large enough to preclude amplification. When the undesired amplification occurs, an extra step is necessary to separate the amplification products by size in order to weed out contaminants.

Another way of reducing or eliminating amplification of contaminating DNA is taking advantage of introns by designing a primer that spans the junction of two exons. In that case, the primer would not be able to anneal and form a stable hybrid with the genomic DNA sequence due to the presence of the intron between the 5'-portion and the 3'-portion of the primer-template hybrid. Unfortunately, in practice, such a method is not always successful. In some instances, stable hybrids form between the genomic DNA and the primer spanning an intron. This may happen either due to "looping out" of the intron, or due to sufficient similarity between the 3'-end of primer and the intron sequence. As illustrated by the Examples (Table 1), genomic DNA is readily amplified by PCR in the presence of at least one primer spanning the exon-exon junction.

It has been discovered that the specificity of an exon-exon junction spanning primer towards mRNA can be greatly improved by certain chemical modifications.

Amplification primers with chemically modified nucleotides have recently been reported. For example, primers comprising modified nucleotides, specifically at nucleotide with a base covalently modified at the exocyclic amino group have been described in U.S. Pat. No. 6,001,611. The synthesis of such nucleotides, and oligonucleotides incorporating such nucleotides are also described in the U.S. Pat. No. 6,001,611.

In one embodiment, the present invention involves an oligonucleotide for selective amplification of a messenger RNA (mRNA) target, comprising an exon-exon junction, in the presence of the corresponding genomic DNA contaminant. The oligonucleotide comprises a sequence at least partially complementary to said mRNA target and spanning the exon-exon junction in the target and further at least one nucleotide with a base covalently modified at the exocyclic amino group.

The present invention involves generally the design and use of oligonucleotide primers to selectively amplify specific regions of target nucleic acid. The parameters for design of amplification primers is familiar to those of skill in the art. Programs useful for such design include, e.g., Visual OMP (DNA Software, Inc., Ann Arbor, Mich.), Oligo 6 (Stratagene, La Jolla, Calif.), Sequencher (Gene Codes, Ann Arbor, Mich.), and DNAStar (DNAStar, Inc., Madison, Wis.).

The present invention involves the use of at least one primer with at least one nucleotide with a base chemically modified at the exocyclic amino group. Preferably, the modified primer is the exon-exon-junction-spanning primer. The nucleotides with covalent modifications of the exocyclic amino groups have been described in U.S. Pat. No. 6,001,611, which is incorporated herein by reference. The synthesis of such nucleotides, and oligonucleotides incorporating such nucleotides is also described in the '611 patent.

According to the present invention, a suitable modification of the exocyclic amino group may be selected based on the presence of the following properties: (1) the modification interferes with but does not prevent Watson-Crick base pairing of the modified base with the complementary base in the double-stranded nucleic acid; (2) the modification interferes with but does not prevent the extension of the primer comprising the modified base by the reverse transcribing enzyme utilizing the mRNA template; (3) the modification allows synthesis of the strand complementary to the strand incorporating the modified base; and (4) the modification increases selectivity of a primer incorporating the modification towards the mRNA template over the DNA template.

The examples of exocyclic amino groups include the amino groups in the 6-position of adenosine, 2-position of guanosine and 4-position of cytidine. Exocyclic amino groups that take part in base pairing with the complementary nucleic acid strand may also occur in various unconventional nitrogenous bases in nucleotides. Examples of nucleosides with unconventional bases include, without limitation, 3-methyladenosine, 7-methylguanosine, 3-methylguanosine, 5-methylcytidine, and 5-hydroxymethylcytidine. Suitable modifications of exocyclic amino groups of such unconventional bases may also be selected according to the empirical method of the present invention.

The structures of the modified nucleotides comprising a modified adenine, guanine, and cytosine base, respectively, are shown below,

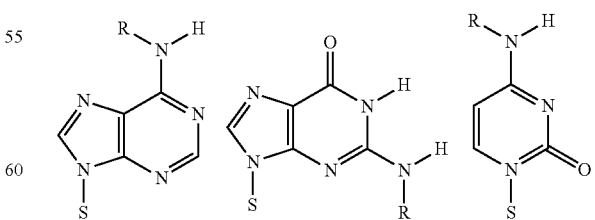

where S represents the sugar moiety, and R represents the modifier group. A variety of modifier groups are envisioned which possess the four properties outlined above. In certain embodiments, modifier groups have the structure:

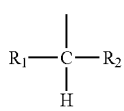

wherein $R_1$ and $R_2$ are independently selected from the group consisting of hydrogen, alkyl, alkoxy, unsubstituted or substituted aryl and phenoxy.

Alkyl groups may be branched or unbranched

Alkyl groups can be $C_1$-$C_{20}$ alkyls, for example $C_1$-$C_{10}$ alkyls.

Alkoxy groups can be $C_1$-$C_{20}$ alkoxy, for example $C_1$-$C_{10}$ alkoxy.

Aryl can be unsubstituted or substituted phenyl or naphtyl.

In one embodiment, R is a benzyl group or a substituted benzyl group. In certain embodiments, substituted benzyl groups can have the following structure:

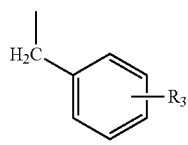

wherein $R_3$ represents a $C_1$-$C_6$ branched or unbranched alkyl group, more preferably a $C_1$-$C_4$ branched or unbranched alkyl group, an alkoxy group, or a nitro group. Preferably, $R_3$ is attached in the para-position.

In some embodiments, the modifier groups are represented by structures shown below:

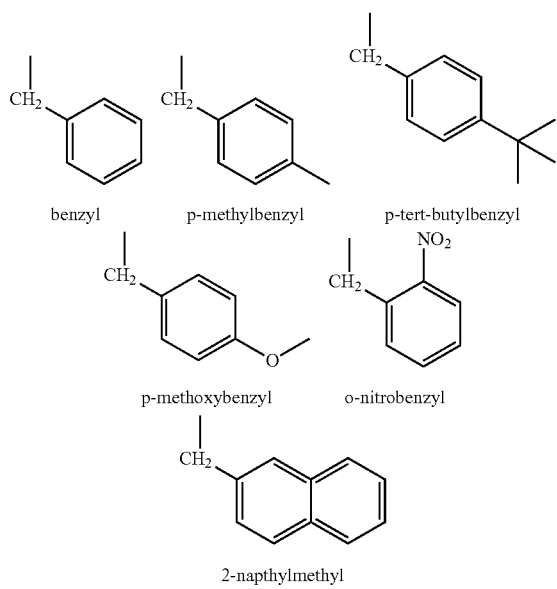

In general, empirical selection of a particular suitable modifier group from the class of compounds described herein can be carried out routinely by one of skill in the art, based on the presence of the four properties listed above. Preferably, suitability of a particular group is determined empirically by using the primers with modified nucleotides in an mRNA amplification reaction as compared to a DNA amplification reaction. The suitability of the modification is indicated by the amplification of the mRNA template and a lack or a substantial delay of detectable amplification of the corresponding DNA template when a modified primer is used. Increased selectivity of the reaction is observed by utilizing a primer with the base modification, when compared to an identical reaction with an unmodified primer.

In another embodiment, the present invention is a method of selective amplification of a messenger RNA (mRNA) target, comprising an exon-exon junction, in the presence of the corresponding genomic DNA contaminant. The method comprises providing a sample, which possibly comprises the target messenger RNA, but may also contain corresponding genomic DNA; a) hybridizing a first oligonucleotide to said mRNA target and performing RNA-directed DNA synthesis using at least one enzyme capable of RNA-directed synthesis, wherein said first oligonucleotide comprises at least one nucleotide modified at the exocyclic amino group, is at least partially complementary to said mRNA target, and spans an exon-exon junction in the target; and b) amplifying the product of step a) using said first oligonucleotide and a second oligonucleotide with at least one enzyme capable of DNA-directed DNA synthesis; wherein said second oligonucleotide is at least partially complementary to said mRNA target.

The method of the present invention utilizes polymerase chain reaction (PCR) for the amplification of target nucleic acid sequences. In particular, to amplify an mRNA target, the methods utilize reverse transcription—polymerase chain reaction (RT-PCR). In some embodiments, the method of the invention utilizes "real-time," or "kinetic" PCR. Typically, kinetic PCR is performed in the presence of at least two primers and a labeled oligonucleotide probe to enable detection of the amplified product during amplification. In some embodiments, the probe is a hybridization probe which emits detectable signal upon hybridization to the target sequence during each cycle of amplification. In other embodiments, the probe is a nuclease probe which emits the signal upon 5'-3'-nuclease digestion of the hybridized probe by the DNA polymerase during each cycle of amplification.

In some embodiments, the RT-PCR reaction involves a hot start protocol. In the context of RT-PCR, the selectivity of the primers with respect to RNA and corresponding DNA may be enhanced by the use of a hot start protocol. Many hot start protocols are known in the art, for example, the use of wax, separating the critical reagents from the rest of the reaction mixture (U.S. Pat. No. 5,411,876), the use of a nucleic acid polymerase, reversibly inactivated by an antibody (U.S. Pat. No. 5,338,671), a nucleic acid polymerase reversibly inactivated by an oligonucleotide that is designed to specifically bind its active site (U.S. Pat. No. 5,840,867) or the use of a nucleic acid polymerase with reversible chemical modifications, as described e.g. in U.S. Pat. Nos. 5,677,152 and 5,773,528.

In some embodiments of the invention, the RT-PCR assay includes the real-time PCR assay. In a real-time PCR assay, the measure of amplification is the "threshold cycle" or Ct value. An earlier Ct value reflects the rapid achievement of the threshold level and thus a more efficient amplification or a higher input of the target nucleic acid. The later Ct value may reflect inefficient or inhibited amplification or a lower input of the target nucleic acid. In the context of the RNA-specific amplification assay, the higher Ct value corresponding to the DNA target is a measure of discrimination between the RNA and DNA targets or the selectivity of the assay.

The RT-PCR assay may employ any suitable thermostable nucleotide-incorporating enzyme known in the art as well as non-thermostable enzymes such as for example MMLV RT and AMV RT. It is sometimes desirable to use an enzyme without the proof-reading (3'-5'-exonuclease) activity, such as for example, Taq DNA polymerase, such as for example rTth or Z05. It may also be desirable to use enzymes, substantially or entirely lacking the 5'-3' nuclease activity, such as described in U.S. Pat. No. 5,795,762. One example of such an enzyme is ΔZ05 polymerase. It may sometimes be desirable to have an enzyme with a "hot start" capability, such as the reversibly modified enzymes described in U.S. Pat. Nos. 5,677,152 and 5,773,528. One example of a hot-start enzyme is ΔZ05-Gold polymerase. In some embodiments, a modified enzyme with desirable engineered properties may also be used.

Detection of the amplification products may be accomplished by any method known in the art. These methods include the use of labeled primers and probes as well as various nucleic acid-binding dyes. The means of detection may be specific to one variant of the target sequence, or may be generic to all variants of the target sequence or even to all double stranded DNA. The non-specific detection methods may be used where the amplification of the undesired variants of the target is minimal and expected to fall below the detection limit of the method.

The amplification products may be detected after the amplification has been completed, for example, by gel electrophoresis of the unlabeled products and staining of the gel with a nucleic acid-binding dye. Alternatively, the amplification products may carry a radioactive or a chemical label, either by virtue of incorporation during synthesis or by virtue of being the extension products of a labeled primer. After, or during electrophoresis, the labeled amplification products may be detected with suitable radiological or chemical tools known in the art. After electrophoresis, the product may also be detected with a target-specific probe labeled by any one of the methods known in the art. The labeled probe may also be applied to the target without electrophoresis, i.e. in a "dot blot" assay or the like.

In other embodiments, the presence of the amplification product may be detected in a homogeneous assay, i.e. an assay where the nascent product is detected during the cycles of amplification, or at least in the same unopened tube, and no post-amplification handling is required. A homogeneous amplification assay has been described for example, in U.S. Pat. No. 5,210,015. Homogeneous amplification assay using nucleic acid-intercalating dyes has been described for example, in U.S. Pat. Nos. 5,871,908 and 6,569,627. The homogeneous assay may also employ fluorescent probes labeled with two interacting fluorophores, such as "molecular beacon" probes (Tyagi et al., (1996) *Nat. Biotechnol.,* 14:303-308) or fluorescently labeled nuclease probes (Livak et al., (1995) *PCR Meth. Appl.,* 4:357-362). In certain variations of these technologies, an amplification product may also be identified by virtue of its distinctive melting temperature, see U.S. Pat. Nos. 5,871,908 and 6,569,627.

In the case of homogeneous amplification, the target is detected with the use of an oligonucleotide probe. The probe is labeled with a label that facilitates the determination of the presence or identity of the target. The probe can comprise one or more label moiety, and optionally one or more quencher moiety. The label moiety may be one detectable by spectroscopic, photochemical, biochemical, immunochemical or chemical means.

In some embodiments the label is a fluorescent moiety. Fluorescent labels can include dyes that are negatively charged, such as dyes of the fluorescein family, or dyes that are neutral in charge, such as dyes of the rhodamine family, or dyes that are positively charged, such as dyes of the cyanine family. Other families of dyes that can be used in the invention include, e.g., polyhalofluorescein-family dyes, hexachlorofluorescein-family dyes, coumarin-family dyes, oxazine-family dyes, thiazine-family dyes, squarine-family dyes, chelated lanthanide-family dyes, ALEXA FLUOR® dyes BODIP®-family dyes (Molecular Probes, Inc., Eugene, Oreg.).

In addition to fluorescent labels, the probes may have one or more quencher moieties. A quencher refers to a chemical moiety that absorbs energy emitted from a fluorescent dye, or otherwise interferes with the ability of the fluorescent dye to emit light. A quencher may re-emit the energy absorbed from a fluorescent dye in a signal characteristic for that quencher. Alternatively, a quencher may dissipate the energy absorbed from a fluorescent dye as heat. Exemplary non-fluorescent quenchers include the Black Hole Quenchers™ marketed by Biosearch Technologies, Inc. (Novato, Calif.), Eclipse Dark Quenchers from Epoch Biosciences (Bothell, Wash.), and Iowa Black (Integrated DNA Technologies, Coralville, Iowa).

The labels and quenchers can be attached to the oligonucleotide probe directly or indirectly by a variety of techniques. Depending on the precise type of label used, the label might be located at the 5'-end or 3'-end of the probe, or be located internally in the nucleotide sequence. The labels and quenchers may be attached directly to a nucleotide, or may be attached indirectly via linkers or spacers. Preparation of labeled oligonucleotides from commercially available reagents such as phosphoramidites is described in *PCR Protocols: A Guide to Methods and Applications,* ed. by Innis et al., Academic Press, Inc., 1990.

In another embodiment, the invention provides a reaction mixture for specifically or selectively amplifying mRNA in the presence of corresponding genomic DNA contaminant, the mixture comprising at least one first oligonucleotide, at least partially complementary to said mRNA target and spanning the exon-exon junction in the target; wherein said first oligonucleotide comprises at least one nucleotide with a base modified at the exocyclic amino group; and at least one second oligonucleotide, at least partially complementary to said mRNA target. The reaction mixture may further comprise one or more enzymes capable of RNA-directed and DNA-directed DNA synthesis. The reaction mixture may further comprise the reagents and solutions generally necessary for the amplification of nucleic acids, including nucleic acid precursors, i.e. nucleoside triphosphates, and organic and inorganic ions, suitable for the support of the activity of the enzymes present in the reaction mixture. The reaction mixture may further comprise the target mRNA. The reaction mixture may further comprise the corresponding genomic DNA. Yet further, the reaction mixture may comprise reagents necessary for detection of amplified nucleic acids.

In another embodiment, the invention provides a kit for specifically or selectively amplifying mRNA in the presence of corresponding genomic DNA contaminant, the kit including at least one first oligonucleotide, at least partially complementary to said mRNA target and spanning the exon-exon junction in the target; wherein said first oligonucleotide comprises at least one nucleotide with a base modified at the exocyclic amino group; and at least one second oligonucleotide, at least partially complementary to said mRNA target. The kit may also include one or more enzymes capable of RNA-directed and DNA-directed DNA synthesis. The kit may further include the reagents and solutions generally necessary for the amplification of nucleic acids, including nucleic acid precursors, i.e. nucleoside triphosphates, and organic and inorganic ions, suitable for the support of the activity of the enzymes present in the kit. The kit may further include an amount of target mRNA. The kit may further include an amount of the corresponding genomic DNA. Yet further, the kit may include reagents necessary for detection of amplified nucleic acids. Yet further, the kit may include instructions for practicing the method of the present invention.

The following examples are provided to aid the understanding of the present invention, the true scope of which is set forth in the appended claims. It is understood that modifications can be made in the procedures set forth without departing from the spirit of the invention.

EXAMPLES

In the following examples, each 50 μl reaction contained 10 ng, 100 ng, or 1 μg of human genomic DNA, or 10 ng or 100 ng of ffpet RNA as template. In some experiments, a positive control reagent containing a mixture of in-vitro RNA transcripts was used as a template. The different templates are described in the results tables. Separate reactions containing each of the different reverse primers were combined with a common forward primer and a common probe. Each reaction contained 0.3 μM of each forward and reverse primer, 0.1 μM of probe, 2.5 mM manganese acetate, 50 mM tricine, 150 mM potassium acetate, 13.4 mM potassium hydroxide, 8% glycerol, 1% DMSO, 200 μM each dATP, dCTP, dGTP, 400 μM dUTP, 50 μM dTTP, 0.075 μM Hawk Z05, 0.2 U/μl Z05 polymerase, 0.04 U/μl UNG, 0.018% sodium azide, 0.01% Tween-20, and 0.1 mM EDTA.

Reverse transcription (RT) and amplification was performed using the Roche LightCycler 480 instrument. The reactions were subjected to the following temperature profile: 50° C. for 5 minutes (UNG step), 95° C. for 1 minute (polymerase activation), 61° C. for 30 minutes (RT step), followed by 55 cycles of 95° C. for 15 seconds and 61° C. for 30 seconds. Fluorescence data was collected at the end of each 61° C. step for the last 53 cycles to generate growth curves (not shown). Finally, the reactions were cooled to 40° C. for 30 seconds.

TABLE 1

Primers and probes

| oligonucleotide | SEQ ID NO | function | sequence |
|---|---|---|---|
| GB_ERBB2F1 | 1 | Forward primer | CAGTACCCCTGCCCTC TGAGX |
| RL_ERBB2_HEX_3 | 2 | Probe | ECCCCCTGQACCTGCA GCCCCCAP |
| GB_ERBB2R1 | 3 | Reverse primer | GAACATCTGGCTGGTT CACATATTCX |
| LS_ERBB2_R1 | 4 | Reverse primer | CATCTGGCTGGTTCAC ATATTCAG |
| LS_ERBB2_R2 | 5 | Reverse primer | CATCTGGCTGGTTCAC ATATTCAGG |
| LS_ERBB2_R3 | 6 | Reverse primer | CTGGCTGGTTCACATA TTCAGGC |
| LS_ERBB2_R7 | 7 | Reverse primer | TGGCTGGTTCACATAT TCAGGCT |
| LS_ERBB2_R8 | 8 | Reverse primer | GGCTGGTTCACATATT CAGGCTG |
| LS_ERBB2_R9 | 9 | Reverse primer | GCTGGTTCACATATTC AGGCTGG |

TABLE 1-continued

Primers and probes

| oligonucleotide | SEQ ID NO | function | sequence |
|---|---|---|---|
| LS_ERBB2_R10 | 10 | Reverse primer | TGGCTGGTTCACATAT TCAGGY |
| LS_ERBB2_R12 | 11 | Reverse primer | TGGCTGGTTCACATAT TYAGGY |
| LS_ERBB2_R13 | 12 | Reverse primer | TGGCTGGTTCACATAT TCAGGC |
| IS_ERBB2_R14 | 13 | Reverse primer | TGGCTGGTTCACATAT TYAGGC |
| LS_ERBB2_R15 | 14 | Reverse primer | TGGCTGGTTCACATAT TCXGGC |
| LS_ERBB2_R16 | 15 | Reverse primer | TGGCTGGTTCACATAT TCXGGY |

E = cx-HEX
Q = BHQ-2
P = Phosphate
X = N$^6$-para-tert-butyl benzyl-dA
Y = N$^4$-para-tert-butyl benzyl-dC Example 1

Break-through Amplification of Genomic DNA with mRNA Specific Primers

In this example, the amplification of the erbB2 target utilized the forward primer (SEQ ID NO: 1), the reverse primer (SEQ ID NOs: 3), and the detection probe (SEQ ID NO: 2). The forward primer and the probe are located in Exon 30, while the reverse primer spans the junction of Exon 30 and Exon 31 of the erbB2 gene. The template nucleic acid was human genomic DNA purchased from Roche (material #11691112001).

The results are shown in Table 2 as Ct values for the amplification reactions. The results demonstrate that the prior art strategy of avoiding amplification of the DNA contaminant is inadequate. Genomic DNA is readily amplified with the mRNA-specific reverse primer that spans an exon-exon junction.

TABLE 2

Amplification (Ct*) of genomic DNA with mRNA-specific primers

| Seq ID No of Reverse Primer | 1 μg genomic DNA | 100 ng genomic DNA |
|---|---|---|
| 3 | 23.12 (0.14) | 26.83 (0.27) |

*Mean of five experiments, (standard deviation)

Example 2

Improvement of RNA-specific Amplification with mRNA Specific Primers Comprising More Bases Complementary to Exon 30.

In this example, the amplification of the erbB2 target utilized the forward primer (SEQ ID NO: 1), a reverse primer selected from SEQ ID NOs: 3-6 and the detection probe (SEQ ID NO: 2). The forward primer and the probe are located in Exon 30, while the reverse primer spans the junction of Exon 30 and Exon 31 of the erbB2 gene and comprises more bases complementary to Exon 30 than does reverse primer with SEQ ID No 3. The templates used were human genomic DNA, DNA isolated from formalin-fixed, paraffin embedded tissue (FFPET), and RNA isolated from FFPET. The results are shown in Table 3 as Ct values for the amplification reactions. The Ct difference between the RNA and the DNA template is indicative of a greater specificity of the assay towards the RNA template. The reverse primer with SEQ ID No: 6 showed the greatest improvement in specificity towards the RNA template.

TABLE 3

Amplification (Ct*) of RNA and DNA templates

| Seq ID No of reverse primer | 10 ng genomic DNA | 10 ng FFPET-DNA | 10 ng FFPET-RNA |
|---|---|---|---|
| 3 | 30.75 (0.42) | 38.25 (0.64) | 27.16 (0.05) |
| 4 | 27.65 (0.18) | 34.85 (0.22) | 26.76 (0.06) |
| 5 | 29.77 (0.17) | 36.19 (0.45) | 26.71 (0.30) |
| 6 | 37.74 (0.72) | 36.23** | 26.66 (0.16) |

*Average of three experiments, (standard deviation)
**One of three experiments gave detectable results.

Example 3

Further Improvement of RNA-specific Amplification with mRNA Specific Primers Primers Comprising More Bases Complementary to Exon 30.

In this example, the amplification of the erbB2 target utilized the forward primer (SEQ ID NO: 1), a reverse primer selected from SEQ ID NOs: 6-9, and the detection probe (SEQ ID NO: 2). The forward primer and the probe are located in Exon 30, while the reverse primer spans the junction of Exon 30 and Exon 31 of the erbB2 gene and comprises more bases complementary to exon 30 than does reverse primer with SEQ ID No: 3. The templates used were human genomic DNA, RNA isolated from FFPET, and a positive control reagent which is a blend of RNA transcripts providing 16 copies/µl of ERBB2 in-vitro RNA transcript in the reaction.

The results are shown in Tables 4 and 5 as Ct values for the amplification reactions. The Ct difference between the RNA and the DNA template is indicative of a greater specificity of the assay towards the RNA template, with a result of ND (not detectable) indicating no amplification of the template. The reverse primer with SEQ ID No: 7 shows the greatest improvement of specificity towards the RNA template.

TABLE 4

Amplification (Ct*) of RNA and DNA templates

| Seq ID No of reverse primer | 100 ng genomic DNA | 10 ng genomic DNA | Positive control RNA |
|---|---|---|---|
| 3 | 26.69 (0.05) | 30.41 (0.19) | 29.72 (0.20) |
| 6 | 34.89 (0.19) | 39.12 (2.04) | 29.72 (0.20) |
| 7 | 36.14** | ND | 29.75 (0.04) |

TABLE 4-continued

Amplification (Ct*) of RNA and DNA templates

| Seq ID No of reverse primer | 100 ng genomic DNA | 10 ng genomic DNA | Positive control RNA |
|---|---|---|---|
| 8 | 31.90 (0.07) | 34.93 (0.65) | 29.81 (0.10) |
| 9 | 30.15 (0.03) | 33.36 (0.51) | 29.60 (0.07) |

*Average of three experiments, (standard deviation)
**One of three experiments gave detectable results.

TABLE 5

Amplification (Ct) of RNA and DNA templates

| Seq ID No of reverse primer | 100 ng genomic DNA* | 100 ng FFPET RNA** |
|---|---|---|
| 3 | 27.23* (0.20) | 23.73 (0.13) |
| 6 | 35.79 (0.47) | 23.23 (0.30) |
| 7 | 35.54 (0.70)*** | 23.16 (0.08) |

*Average of six experiments, (standard deviation)
**Average of three experiments, (standard deviation)
***Three of six experiments gave detectable results.

Example 4

Improvement of RNA-specific Amplification with mRNA Specific Primers Comprising a Modification.

In this example, the amplification of the erbB2 target utilized the forward primer (SEQ ID NO: 1), a reverse primer selected from SEQ ID NOs: 3-10, and the detection probe (SEQ ID NO: 2). The forward primer and the probe are located in Exon 30, while the reverse primer spans the junction of Exon 30 and Exon 31 of the erbB2 gene and comprises more bases complementary to exon 30 than does reverse primer with SEQ ID No 3. Reverse primer with SEQ ID No: 10 comprises a modification. The templates used were human genomic DNA and a positive control reagent which is a blend of RNA transcripts providing 16 copies/µl of in-vitro RNA ERBB2 transcript in the reaction.

The results are shown in Table 6 as Ct values for the amplification reactions. The Ct difference between the RNA and the DNA template is indicative of a greater specificity of the assay towards the RNA template, with a result of ND (not detectable) indicating no amplification of the template. The reverse primer with SEQ ID No: 10 comprises a modification and shows the greatest improvement of specificity towards the RNA template.

TABLE 6

Amplification (Ct) of RNA and DNA templates

| Seq ID No of reverse primer | 100 ng genomic DNA* | Positive control RNA** |
|---|---|---|
| 3 | 26.91 (0.14) | 30.24 (0.09) |
| 7 | 34.43 (0.39)*** | 29.95 (0.03) |
| 10 | ND | 30.39 (0.05) |

*Average of six experiments, (standard deviation)
**Average of three experiments, (standard deviation)
***Three of six experiments gave detectable results. Average of three experiments, (standard deviation)

Example 5

Improvement of RNA-specific Amplification with mRNA Specific Primers Comprising a Modification.

In this example, the amplification of the erbB2 target utilized the forward primer (SEQ ID NO: 1), a reverse primer selected from SEQ ID NOs: 7-10, and the detection probe (SEQ ID NO: 2). The forward primer and the probe are located in Exon 30, while the reverse primer spans the junction of Exon 30 and Exon 31 of the erbB2 gene and comprises a modification. The templates used were human genomic DNA, RNA isolated from FFPET, and a positive control reagent which is a blend of RNA transcripts providing 16 copies/µl of ERBB2 in-vitro RNA transcript in the reaction.

The results are shown in Table 7 as Ct values for the amplification reactions. The Ct difference between the RNA and the DNA template is indicative of a greater specificity of the assay towards the RNA template. The reverse primer with SEQ ID No: 10 comprises a modification and shows the greatest improvement of specificity towards the RNA template.

TABLE 7

Amplification (Ct*) of RNA and DNA template

| Seq ID No of reverse primer | 1 µg genomic DNA* | 100 ng FFPET RNA** | Positive control RNA** |
|---|---|---|---|
| 7 | 33.08 (0.30) | 22.97 (0.04) | 29.94 (0.07) |
| 10 | 42.43*** | 23.81 (0.17) | 30.58 (0.19) |

*Average of five experiments, (standard deviation)
**Average of three experiments, (standard deviation)
***One of five experiments gave detectable results.

Example 6

Improvement of RNA-specific Amplification with mRNA Specific Primers Comprising a Modification.

In this example, the amplification of the erbB2 target utilized the forward primer (SEQ ID NO: 1), a reverse primer selected from SEQ ID NOs: 3, 6, 7, 10, 11, 12, 13, 14 and 15 and the detection probe (SEQ ID NO: 2). The forward primer and the probe are located in Exon 30, while the reverse primer spans the junction of Exon 30 and Exon 31 of the erbB2 gene and comprises a modification. The templates used were human genomic DNA and RNA isolated from FFPET. The results are shown in Table 8 as Ct values for the amplification reactions. The Ct difference between the RNA and the DNA template is indicative of a greater specificity of the assay towards the RNA template. The reverse primer with SEQ ID No: 10 comprises a modification and shows the greatest improvement in specificity towards the RNA template. Reverse primers with SEQ ID No: 11 and SEQ ID No: 15 also show improvement in specificity towards the RNA template; however, the Ct values for the RNA FFPET template are delayed as compared to results obtained with SEQ ID No: 10.

TABLE 8

Amplification (Ct*) of DNA and RNA templates

| Seq ID No of reverse primer | 100 ng genomic DNA | 100 ng FFPET RNA |
|---|---|---|
| 3 | 27.37 (0.29) | 24.23 (0.07) |
| 6 | 34.37 (0.28) | 23.60 (0.12) |
| 7 | 34.88 (0.24) | 23.57 (0.01) |
| 10 | ND | 24.23 (0.04) |
| 11 | ND | 29.43 (0.05) |
| 12 | 35.46 (0.84) | 23.61 (0.03) |
| 13 | 44.16 (5.43)** | 24.60 (0.01) |
| 14 | 40.92 (0.37)** | 24.26 (0.10) |
| 15 | ND | 30.04 (0.10) |

*Average of three experiments, (standard deviation)
**Two of three experiments gave detectable results. Average of two experiments, (standard deviation)

Amplification curves for the primers SEQ ID: Nos 3, 6, 7, 10, 11, 12, 13, 14 and 15 can respectively be found on FIGS. 3, 4, 5, 6, 7, 8, 9, 10 and 11.

While the invention has been described in detail with reference to specific examples, it will be apparent to one skilled in the art that various modifications can be made within the scope of this invention. Thus the scope of the invention should not be limited by any of the examples described herein, but by the claims presented below. All publications including patent applications and patents cited in this application are incorporated by reference in their entirety for all purposes to the same extent as if each individual publications were individually indicated to be incorporated by reference for all purposes.

The invention claimed is:

1. A method of selective amplification of a messenger RNA (mRNA) target in the presence of corresponding genomic DNA contaminant comprising the steps of:
   a. providing a sample that comprises said mRNA target and said corresponding genomic DNA contaminant
   b. hybridizing a first oligonucleotide to said mRNA target and performing RNA-directed DNA synthesis using at least one enzyme capable of RNA-directed synthesis, wherein said first oligonucleotide:
      i. comprises at least one nucleotide with a base covalently modified at the exocyclic amino group,
      ii. is at least partially complementary to said mRNA target and to said corresponding genomic DNA contaminant, and,
      iii. spans an exon-exon junction in the target;
   c. amplifying the product of step b) using said first oligonucleotide and a second oligonucleotide with at least one enzyme capable of DNA-directed DNA synthesis; wherein said second oligonucleotide is at least partially complementary to said mRNA target and to said corresponding genomic DNA contaminant;
   wherein said mRNA target is selectively amplified over said corresponding genomic DNA contaminant when compared to amplifying with an unmodified first oligonucleotide.

2. The method of claim 1, wherein the base covalently modified at the exocyclic amino group of the nucleotide is selected from a group consisting of N6-benzyl-adenine, N6-para-tert-butyl-benzyl adenine, N4-para-tert-butyl-benzyl cytosine, N2-alkyl-guanine and N4-benzyl-cytosine.

3. The method of claim 1, further comprising a step d of detecting the product of said RNA-directed and DNA-directed DNA synthesis.

4. The method of claim 1, wherein the enzyme capable of RNA-directed synthesis and the enzyme capable of DNA-directed DNA synthesis are the same.

5. The method of claim 1 wherein said one or more enzymes are substantially lacking the 5'-3' nuclease activity.

6. The method of claim 1, wherein said at least one enzyme is selected from the group consisting of Taq DNA polymerase, Z05 DNA polymerase, delta-Z05 DNA polymerase and delta-Z05-Gold DNA polymerase or mutants thereof.

7. The method of claim 1, wherein said first oligonucleotide is selected from a group consisting of SEQ ID NOs: 3, 10, 11, 13, 14 and 15.

\* \* \* \* \*